United States Patent
Nayar

(10) Patent No.: US 9,687,549 B2
(45) Date of Patent: *Jun. 27, 2017

(54) TOPICAL PHARMACEUTICAL GEL COMPOSITION OF DICLOFENAC SODIUM

(71) Applicant: Gavis Pharmaceuticals, Somerset, NJ (US)

(72) Inventor: Bala Chandran Nayar, Somerset, NJ (US)

(73) Assignee: Lupin Atlantis Holdings SA, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/056,853

(22) Filed: Feb. 29, 2016

(65) Prior Publication Data

US 2016/0263029 A1 Sep. 15, 2016

Related U.S. Application Data

(60) Provisional application No. 62/133,333, filed on Mar. 14, 2015.

(51) Int. Cl.

| | | |
|---|---|---|
| *A61K 31/196* | (2006.01) | |
| *A61K 9/06* | (2006.01) | |
| *A61K 47/02* | (2006.01) | |
| *A61K 47/14* | (2017.01) | |
| *A61K 47/32* | (2006.01) | |
| *A61K 9/00* | (2006.01) | |
| *A61K 47/10* | (2017.01) | |
| *A61K 47/18* | (2017.01) | |

(52) U.S. Cl.
CPC ............ *A61K 47/02* (2013.01); *A61K 9/0014* (2013.01); *A61K 31/196* (2013.01); *A61K 47/10* (2013.01); *A61K 47/14* (2013.01); *A61K 47/183* (2013.01); *A61K 47/32* (2013.01)

(58) Field of Classification Search
IPC .......................... A61K 47/02, 47/10, 47/14, 9/06
See application file for complete search history.

(56) References Cited

U.S. PATENT DOCUMENTS

| | | | | |
|---|---|---|---|---|
| 2007/0269393 A1* | 11/2007 | Wepfer | ................... | A61K 9/06 424/59 |
| 2012/0220962 A1* | 8/2012 | Hsu | ...................... | A61K 9/0014 604/307 |

FOREIGN PATENT DOCUMENTS

WO  WO 2006/134406  * 12/2006 ........... A61K 9/0014

* cited by examiner

*Primary Examiner* — Shirley V Gembeh

(74) *Attorney, Agent, or Firm* — William D. Hare; McNeely Hare & War, LLP

(57) ABSTRACT

A topical pharmaceutical gel compositions of diclofenac sodium, is provided. The topical gel composition contains at least about 10% w/w diclofenac sodium and is suitable for twice daily application.

18 Claims, No Drawings

TOPICAL PHARMACEUTICAL GEL COMPOSITION OF DICLOFENAC SODIUM

CROSS-REFERENCE TO RELATED APPLICATIONS

This application is a nonprovisional application claiming the benefit priority of U.S. Provisional Application No. 62/133,333, filed Mar. 14, 2015, the contents of which are incorporated herein in their entirety by reference.

BACKGROUND OF THE INVENTION (a) Field of the Invention

The present invention is directed to novel topical pharmaceutical gel compositions of diclofenac sodium. The topical compositions comprise at least about 10% w/w of diclofenac sodium and are suitable for twice a day application. The invention is further directed to the use of said composition for treatment of painful conditions, inflammations and/or rheumatic diseases or providing relief of the pain of osteoarthritis of joints amenable to topical treatment. Additionally, the present invention provides a method of manufacture of said composition.

(b) Description of the Related Art

Delivery of active agents across the skin or mucosal membrane is convenient, pain-free, non-invasive and circumvents problems associated with the "first pass effect". Such transdermal or topical drug delivery is typically restricted to low molecular weight drugs and drugs with specific lipophilic/hydrophilic balance able to penetrate the stratum corneum.

Transdermal drug delivery systems enable chemical modification of the barrier properties of the skin to effectively and efficiently permit permeation thereof. Known drawbacks of transdermal delivery systems are, for example, the length of time needed for permeation, a frequent dosing regimen, and the volume size of a transdermal composition needed to transdermally deliver a sufficient therapeutic amount of the active agent.

Today, pain has become the universal disorder, a serious and costly public health issue, and a challenge for family, friends, and health care providers who must give support to the individual suffering from the physical as well as the emotional consequences of pain. In general, there are two basic types of pain: acute and chronic. Acute pain, for the most part, results from disease, inflammation, or injury to tissues. This type of pain generally comes on suddenly, for example, after trauma or surgery. In some instances, it can become chronic. Chronic pain is widely believed to represent disease itself. Chronic pain persists over a longer period of time than acute pain and is resistant to most medical treatments. It can, and often does, cause severe problems for patients.

Transdermal non-steroidal anti-inflammatory drugs (NSAIDs) offer the possibility of achieving local therapeutic benefit in pain while reducing or eliminating the risk of systemic side effects. There has been widespread interest in this approach to treating painful conditions, such as osteoarthritis (OA), but data in support of the efficacy of topical NSAIDs in the treatment of OA is limited. For instance, a study of 13 randomized placebo controlled trials of various topical NSAIDs tested specifically for use in the treatment of OA concluded that they were not generally efficacious for chronic use in OA. (Lin et al, Efficacy of topical non-steroidal anti-inflammatory drugs in the treatment of osteoarthritis: meta-analysis of randomized controlled trials, BMJ, 2004).

Diclofenac (2-(2,6-dichloranilino) phenylacetic acid) is a non-steroidal anti-inflammatory drug (NSAID) used to reduce inflammation and, as an analgesic, to reduce pain. It is available in the sodium, potassium, epolamine and diethylamine salt forms in numerous dosage forms (oral tablet, oral syrup, topical gel, cataplasm, ophthalmic drop, suppository, etc.).

An example of a well-known transdermal diclofenac formulation is Voltaren® Gel 1% which comprises 1% diclofenac sodium. Voltaren® is indicated in the USA for the relief of the pain due to osteoarthritis of joints amenable to topical treatment, such as the knees and the hands. Up to 4 grams of Voltaren® gel can be applied to the lower extremities (including the knees, the ankles, and the feet) 4 times daily so that up to not more than 16 grams daily of Voltaren® Gel 1% is applied to any single joint of the lower extremities. Up to 2 grams of Voltaren® Gel 1% can also be applied to the upper extremities (which include the elbows, the wrists and the hands) 4 times daily so that up to not more than 8 grams daily of Voltaren® Gel 1% is applied to any single joint of the upper extremities. Overall, the total dose of Voltaren® Gel 1% should not exceed 32 grams per day over all affected joints. Neither the total amount (up to 32 grams per day) nor the frequency of application (4 times a day) are satisfactory from a patient perspective.

U.S. Pat. No. 7,335,379 discloses formulations for transdermal or transmucosal administration of active agents, such as diclofenac, containing an alkanol, a polyalcohol, a monoalkyl ether of diethylene glycol and a fatty alcohol with a fatty alcohol content of up to 2%.

U.S. Pat. No. 4,543,251 discloses an external gel formulation containing 0.3 to 3% w/w of diclofenac sodium having good stability.

PCT Application Publication No. 2014009241 discloses diclofenac gel formulations containing 1% and 3% diclofenac sodium, $C_2$ to $C_4$ alkanol, monoalkyl ether of diethylene glycol and fatty alcohol.

U.S. Pat. No. 7,132,452 discloses topical formulations containing a NSAID, particularly diclofenac for alleviating the pain/inflammation associated with infection caused by the herpes virus. The amount of diclofenac in the formulation can be 1-10% w/w of the entire formulation. The '452 patent discloses that the formulation provides complete relief on application for seven days.

EP Pat. No. 1,890,687 discloses topical gel formulations of diclofenac sodium for relief of pain and inflammation. According to the patent the formulation may contain up to 10% w/w of diclofenac.

U.S. Pat. Nos. 4,575,515 and 4,652,557 disclose topical NSAID compositions, one of which, consisting of 1.5% diclofenac sodium, 45.5% dimethylsulphoxide, 11.79% ethanol, 11.2% propylene glycol, 11.2% glycerine, and water, has been shown to be effective in chronic OA treatment.

None of the prior art references disclose or suggest topical gel formulations containing a high amount of diclofenac sodium, let alone its therapeutic benefits on twice daily application. Moreover, the known formulation containing lower amounts of diclofenac sodium requires frequent dosing of three to four times a day to achieve efficacy in chronic conditions, such as OA, which can increase the risk of skin irritation.

There remains a need for topical compositions of diclofenac containing at least about 10% w/w of diclofenac sodium which are effective for treatment of painful conditions, such as inflammation. The compositions should provide fast and effective treatment for alleviating symptoms relating to acute or chronic pain, including that of osteoarthritis of joints, and require only twice daily application to achieve equal or more therapeutic benefits than those achieved by multiple applications of currently known 1% w/w or 3% w/w diclofenac gel formulations.

SUMMARY OF THE INVENTION

The present invention provides a topical pharmaceutical gel composition suitable for twice daily application of diclofenac sodium.

In one aspect, the invention provides a topically applicable pharmaceutical gel composition suitable for once-a-day application of diclofenac sodium comprising diclofenac sodium in an amount of at least about 10% w/w of the composition, wherein twice a day application of said pharmaceutical gel composition provides steady state blood levels of diclofenac that are comparable to steady state blood levels of diclofenac achieved with 4 times daily application of diclofenac sodium 1% or 3% w/w topical gel.

In another aspect, twice daily administration of said composition provides steady state blood levels of diclofenac in the range of about 5 ng/ml to about 30 ng/ml.

In another aspect, twice daily administration of said composition provides steady state blood $C_{max}$ levels of diclofenac in the range of about 5 ng/ml to about 50 ng/ml.

In another aspect, twice daily administration of said composition provides steady state blood $C_{min}$ levels of diclofenac in the range of about 5 ng/ml to about 20 ng/ml.

In another aspect, twice daily administration of said composition provides steady state AUC in the range of about 10 ng/ml*hr to about 100 ng/ml*hr.

In another aspect, the topical pharmaceutical gel composition consists of diclofenac sodium as the sole active ingredient and a carrier with the diclofenac sodium being present at a concentration of about 10% w/w, about 12% w/w or about 14% w/w.

In another aspect, the topical pharmaceutical gel composition consists of diclofenac sodium as the sole active ingredient and a carrier with the diclofenac sodium being present at a concentration of 10% w/w, 12% w/w or 14% w/w.

In another aspect, the topical pharmaceutical gel composition consists essentially of diclofenac sodium as the sole active ingredient and a carrier with the diclofenac sodium being present at a concentration of about 10% w/w, about 12% w/w or about 14% w/w.

In another aspect, the topical pharmaceutical gel composition consists essentially of diclofenac sodium as the sole active ingredient and a carrier with the diclofenac sodium being present at a concentration of 10% w/w, 12% w/w or 14% w/w.

In another aspect, the topical pharmaceutical gel composition consists of diclofenac sodium, salicylate ester and menthol as the sole active ingredients and a carrier with the diclofenac sodium being present at a concentration of about 10% w/w, about 12% w/w or about 14% w/w.

In another aspect, the topical pharmaceutical gel composition consists essentially of diclofenac sodium, salicylate ester and menthol as the sole active ingredients and a carrier with the diclofenac sodium being present at a concentration of about 10% w/w, about 12% w/w or about 14% w/w.

In another aspect, the topical pharmaceutical gel composition of diclofenac sodium comprises, consists of or consists essentially of:
  at least about 10% w/w of diclofenac sodium,
  about 5-25% w/w of a glycol solvent,
  about 1-6% w/w of at least one gelling agent,
  about 0.01-0.75% w/w of at least one preservative,
  about 0.01-1% w/w of at least one antioxidant,
  about 1-10% w/w of salicylic acid ester,
  about 0.05-1% w/w of menthol,
  at least 50% w/w of water; and
  at least one acidic and/or basic agent to adjust the pH of the composition to 4-8.

In an embodiment, the amount of diclofenac sodium in the gel composition of the invention is about 10% w/w, about 12% w/w or about 14% w/w.

In an embodiment, the amount of diclofenac sodium in the gel composition of the invention is 10% w/w, 12% w/w or 14% w/w.

In an embodiment, the topical pharmaceutical gel composition is devoid of either $C_2$ to $C_4$ alkanol, monoalkyl ether of diethylene glycol, or fatty alcohol.

Also provided is a topically applicable diclofenac sodium gel composition which is stable at room temperature. Methods of treating painful conditions and inflammations or providing fast and effective treatment for alleviating symptoms relating to pain of osteoarthritis of joints using these compositions are further provided by the invention.

In another aspect, the invention provides a topical pharmaceutical gel composition suitable for twice daily application of diclofenac sodium comprising a glycol solvent selected from the group consisting of propylene glycol, polyethylene glycol, ethylene glycol, butylene glycol, and hexalylene glycol, and mixtures thereof. In one embodiment, the glycol solvent in the gel composition is propylene glycol. In a further embodiment, the amount of glycol solvent present in the gel composition is about 5-25% w/w.

In another aspect, the invention provides a topical pharmaceutical gel composition suitable for twice daily application of diclofenac sodium comprising a gelling agent selected from the group consisting of hydroxypropyl cellulose and carbomers and combinations thereof. In one embodiment, the gelling agent in the gel composition is carbomer. In a further embodiment, the amount of gelling agent present in the gel composition is about 1-6% w/w.

In another aspect, the invention provides a topical pharmaceutical gel composition suitable for twice daily application of diclofenac sodium comprising preservatives selected from the group consisting of methyl paraben, propyl paraben, chlorocresol, thomersal, sorbic acid, potassium sorbate and mixtures thereof. In one embodiment, the preservatives in the gel composition are methyl paraben and propyl paraben. In a further embodiment, the amount of preservatives present in the gel composition is about 0.01-0.75% w/w.

In another aspect, the invention provides a topical pharmaceutical gel composition suitable for twice daily application of diclofenac sodium comprising an antioxidant selected from the group consisting of edetate disodium, sodium metabisulfite, propyl gallate, and edetate trisodium, and mixtures thereof. In one embodiment, the antioxidant in the gel composition is edetate disodium. In a further embodiment, the amount of antioxidant present in the gel composition is about 0.01-1% w/w.

In another aspect, the invention provides a topical pharmaceutical gel composition suitable for twice daily application of diclofenac sodium comprising a salicylate ester selected from the group consisting of methyl salicylate, ethyl salicylate and glycol monosalicylate. In one embodiment, the salicylate ester in the gel composition is methyl salicylate. In a further embodiment, the amount of salicylate ester present in the gel composition is about 1-10% w/w.

In another aspect, the invention provides a topical pharmaceutical gel composition suitable for twice daily application of diclofenac sodium comprising propylene glycol, carbomers, edetate disodium, methyl salicylate, menthol and sodium hydroxide.

In another aspect, the topical pharmaceutical gel of the invention is devoid of either $C_2$ to $C_4$ alkanol, monoalkyl ether of diethylene glycol, or fatty alcohol.

In another aspect, viscosity of the topical pharmaceutical gel of the invention is in the range of about 60,000 to 600,000 cps.

In another aspect, the invention provides a process for the manufacture of a topical pharmaceutical gel composition of diclofenac, process comprising the steps of:
(a) dissolving diclofenac sodium, gelling agent, antioxidant and preservative in water;
(b) dissolving preservative, salicylate ester and menthol in a glycol solvent;
(c) adding the solvent mixtures of steps (a) and (b) together and mixing under high shear homogenization; and
(d) adjusting the pH of the mixture with basic and/or acid agent(s) to a pH in the range of about 4 to 6.

In another aspect, the invention provides a method for the treatment of painful conditions, inflammations and/or rheumatic diseases comprising topically applying or administering to a patient in need thereof the gel composition as described herein.

In another aspect, the invention provides a method for the treatment of painful conditions, inflammations and/or rheumatic diseases. The method includes topically applying twice per day a gel composition to a skin surface of a patient in need thereof. The gel composition consists essentially of diclofenac sodium as the sole active ingredient with the diclofenac sodium being present at a concentration of about 10% w/w to about 15% w/w.

In one embodiment, the diclofenac sodium is present at a concentration of about 10% w/w.

Still other aspects and advantages of the invention will be apparent from the following detailed description of the invention.

DETAILED DESCRIPTION OF THE INVENTION

The invention provides for a topical pharmaceutical gel composition suitable for twice daily application of diclofenac sodium. Preferably, the composition contains, at least, a combination of a salicylate ester and menthol along with other components.

The invention addresses the need for a topical gel formulation of diclofenac sodium which requires only twice daily application and provides relief which is comparable to that achieved by 4 times daily application of currently available diclofenac sodium 1% or 3% w/w formulations including Voltaren® 1% Gel.

The invention, for example, provides topical gel formulation of diclofenac sodium containing about 10% w/w to about 15% w/w of diclofenac sodium. The inventors have observed that a particular formulation of diclofenac sodium requires only twice daily application as compared to frequent application required for commercially available diclofenac gel formulations.

The gel composition may be bioequivalent to a topically applied diclofenac sodium that is administered multiple times, e.g., four times per day. Bioequivalence is defined to mean the term used by the drug approval agencies, such as the US Food and Drug Administration: "the absence of a significant difference in the rate and extent to which the active ingredient or active moiety in pharmaceutical equivalents or pharmaceutical alternatives becomes available at the site of drug action when administered at the same molar dose under similar conditions in an appropriately designed study." This is typically understood to mean that the reference drug is within +25% and −20% of the reference drug product for AUC and $C_{max}$, for example as explained in the US FDA's various bioequivalence guidance documents for oral tablets and capsules, which are incorporated herein by reference.

The term "AUC" refers to the area under the time/plasma concentration curve after the administration of the diclofenac sodium dosage form to healthy human subjects. The term "$C_{max}$" refers to the maximum concentration of diclofenac sodium in the blood following the administration of the diclofenac sodium dosage form to healthy human subjects.

In an embodiment, twice daily application of said pharmaceutical gel composition provides steady state blood levels of diclofenac that are comparable to steady state blood levels of diclofenac achieved with 4 times daily application of diclofenac sodium 1% or 3% w/w topical gel.

Twice daily application of said composition provides steady state blood levels of diclofenac in the range of about 5 ng/ml to about 30 ng/ml, steady state blood $C_{max}$ levels of diclofenac in the range of about 5 ng/ml to about 50 ng/ml, steady state blood $C_{min}$ levels of diclofenac in the range of about 5 ng/ml to about 20 ng/ml, and steady state AUC in the range of about 10 ng/ml*hr to about 100 ng/ml*hr.

The inventors have further observed that a topical gel formulation of diclofenac sodium in accordance with the invention is storage stable at a temperature of about 40° C. and relative humidity of about 75% for a period of at least 3 months.

In one embodiment, the topical pharmaceutical gel composition suitable for twice daily application of diclofenac sodium comprises, consists of, or consists essentially of:
at least about 10% w/w of diclofenac sodium,
about 5-25% w/w of a glycol solvent,
about 1-6% w/w of at least one gelling agent,
about 0.01-0.75% w/w of at least one preservative,
about 0.01-1% w/w of at least one antioxidant,
about 1-10% w/w of salicylic acid ester,
about 0.05-1% w/w of menthol,
at least 50% w/w of water, and
at least one acidic and/or basic agent to adjust the pH of the composition to 4-8.

In another embodiment, the amount of diclofenac sodium in the gel composition of the invention is about 10% w/w, about 12% w/w or about 14% w/w.

In a further embodiment, the topical pharmaceutical gel composition is devoid of either $C_2$ to $C_4$ alkanol, monoalkyl ether of diethylene glycol or fatty alcohol.

In an embodiment, the viscosity of the topical pharmaceutical gel composition is in the range of about 60,000 to 600,000 cps.

Suitable glycols include, by way of example and without limitation, propylene glycol, polyethylene glycol, ethylene glycol, butylene glycol, and hexalylene glycol. A preferred glycol is polyethylene glycol. The glycol is preferably present in an amount of about 5-25% w/w.

Suitable gelling agents include, by way of example and without limitation, carbomers, xanthan gum, acacia, tragacanth, sodium alginate, gelatin, modified starches, hydroxypropyl cellulose, hydroxyethyl cellulose, hydroxypropyl methylcellulose, hydroxypropyl methylcellulose phthalate, methyl cellulose, co-polymers formed between maleic anhydride and methyl vinyl ether, methacrylate derivatives, polyethylene oxides, polyoxyethylene-polyoxypropylene copolymers, polyvinyl alcohol and mixtures thereof. A preferred gelling agent is carbomer. The gelling agent is preferably present in an amount of about 1-6% w/w.

Carbomers, in the context of the present invention, are defined as homo- or copolymers of acrylic acid that are cross-linked, e.g., with an allyl ether of pentaerythritol (allyl pentaerythritol) or an allyl ether of sucrose (allyl sucrose). Copolymers are formed, e.g., with minor levels of long chain alkyl acrylate co-monomers. Homopolymers are preferred. Non limiting examples of carbomers are carbomer 940, 971, 973, 974, 980, 981, 941, 974, 934 and 910. Especially preferred are carbomers 980, 940, 981, 941, 974, 934 and 910. Preferably, carbomers are present in an amount of from about 1-6% w/w.

Suitable preservatives include, by way of example and without limitation, methyl paraben, propyl paraben, chlorocresol, thomersal, sorbic acid, potassium sorbate and mixtures thereof. A preferred preservative is a combination of methyl paraben and propyl paraben. The preservatives are preferably present in an amount of about 0.01-0.75% w/w.

Suitable salicylic acid esters include, by way of example and without limitation, methyl salicylate, ethyl salicylate and glycol monosalicylate. A preferred salicylic acid ester is methyl salicylate. The salicylic acid ester is preferably present in an amount of about 0.01-0.75% w/w. In another embodiment, the ratio of the amount of diclofenac sodium to salicylic acid ester is preferably in the range of about 1:0.1 to about 1:0.5.

A suitable antioxidant includes, by way of example and without limitation, edetate disodium, sodium sulphite, sodium metabisulfite, propyl gallate, edetate trisodium, tocopherol derivatives, butylated hydroxyl toluene, butylated hydroxyl anisole, ascorbic acid, fumaric acid, malic acid, and citric acid, and mixtures thereof. A preferred antioxidant is edetate disodium. The antioxidant is preferably present in an amount of about w/w.0.01-1% w/w.

A suitable basic agent includes, by way of example and without limitation, sodium hydroxide, potassium hydroxide and ammonia, and mixtures thereof. A preferred basic agent is sodium hydroxide.

A suitable acidic agent includes, by way of example and without limitation, hydrochloric acid, acetic acid, lactic acid and citric acid, and mixtures thereof. A preferred acidic agent is hydrochloric acid.

In an embodiment, the ratio of amount of diclofenac sodium to menthol is preferably in the range of about 1:0.01 to about 1:0.05.

The topical gel composition of the present invention further may comprise at least one or more additional ingredients or excipients selected from buffering agents, moisturizing agents, humectants, surfactants, neutralizing agents, chelating agents, and emollients.

In an embodiment, the topical pharmaceutical gel composition suitable for twice daily application of diclofenac sodium comprises, consists of, or consists essentially of:
about 10% w/w of diclofenac sodium,
about 10% w/w of propylene glycol,
about 3.5% w/w of carbomer,
about 0.4% w/w of methyl paraben and propyl paraben,
about 0.17% w/w of at least one edetate disodium,
about 3% w/w of methyl salicylate,
about 0.2% w/w of menthol,
at least 50% w/w of water, and
at least one acidic and/or basic agent to adjust the pH of the composition to 4-8.

In an embodiment, the topical pharmaceutical gel composition suitable for twice daily application of diclofenac sodium comprises, consists of, or consists essentially of:
about 14% w/w of diclofenac sodium,
about 20% w/w of propylene glycol,
about 2.5% w/w of carbomer,
about 0.4% w/w of methyl paraben and propyl paraben,
about 0.17% w/w of at least one edetate disodium,
about 7% w/w of methyl salicylate,
about 0.3% w/w of menthol,
at least 50% w/w of water, and
at least one acidic and/or basic agent to adjust the pH of the composition to 4-8.

The composition may be provided with instructions for applying the composition twice daily.

The invention further provides a method for the manufacture of topical gel formulation of diclofenac sodium. The method of manufacture comprises the following steps:
(a) dissolving diclofenac sodium, gelling agent, antioxidant and preservative in water;
(b) dissolving preservative, salicylate ester and menthol in glycol solvent;
(c) adding the solvent mixtures of step (a) and (b) together and mixing under high shear homogenization; and
(d) adjusting the pH of the mixture with a basic and/or acid agent(s) to a pH in the range of about 4 to 6.

In an embodiment, the method for the manufacture of a topical gel formulation of diclofenac sodium comprises the following steps:
(a) dissolving diclofenac sodium, carbomer, edetate sodium and methyl paraben in water;
(b) dissolving propyl paraben, methyl salicylate and menthol in propylene glycol;
(c) adding the solvent mixtures of step (a) and (b) together and mixing under high shear homogenization; and
(d) adjusting the pH with sodium hydroxide and/or hydrochloric acid to a pH in the range of about 4 to 6.

The topical gel formulation of diclofenac sodium of the invention may be topically applied to the affected areas of the skin to a patient suffering from painful conditions, inflammations and/or rheumatic diseases or providing relief of the pain of osteoarthritis of joints.

Compositions of the invention are particularly suited for use in treating osteoarthritis (OA) chronically. They may also be useful for the treatment of other chronic joint diseases characterized by joint pain, degeneration of articular cartilage, impaired movement, and stiffness. Suitable joints include the knee, elbow, hand, wrist and hip.

As the compositions of the invention can be used at twice daily dosing in the treatment of OA, this would represent a significant improvement as lower dosing is associated with better patient compliance, an important factor in treating chronic conditions.

EXAMPLE 1

Diclofenac Sodium 10% w/w Topical Gel

TABLE 1

| Sr. No. | Ingredients | Quantity % w/w |
|---|---|---|
| 1 | Diclofenac Sodium | 10.00 |
| 2 | Carbomer | 3.50 |
| 3 | Edetate Disodium | 0.17 |
| 4 | Methyl paraben | 0.30 |
| 5 | Propyl paraben | 0.08 |
| 6 | Propylene Glycol | 10.00 |
| 7 | Methyl Salicylate | 3.00 |
| 8 | Menthol | 0.10 |
| 9 | Purified Water | QS |
| 10 | Sodium Hydroxide/Hydrochloric Acid (to adjust pH to ~4-6) | QS |

Process: Diclofenac sodium, carbomer, edetate sodium and methyl paraben were dissolved in water. Separately, propyl paraben, methyl salicylate and menthol were dissolved in propylene glycol. The two solutions were added together, mixed under high shear homogenization and the pH of the mixture was adjusted to 4 to 6 with sodium hydroxide and/or hydrochloric acid. The viscosity of the gel measured was in the range of about 60,000 to 600,000 cps.

EXAMPLE 2

Diclofenac Sodium 12% w/w Topical Gel

TABLE 2

| Sr. No. | Ingredients | Quantity % w/w |
|---|---|---|
| 1 | Diclofenac Sodium | 12.00 |
| 2 | Carbomer | 3.00 |
| 3 | Edetate Disodium | 0.17 |
| 4 | Methyl paraben | 0.30 |
| 5 | Propyl paraben | 0.08 |
| 6 | Propylene Glycol | 15.00 |
| 7 | Methyl Salicylate | 5.00 |
| 8 | Menthol | 0.20 |
| 9 | Purified Water | QS |
| 10 | Sodium Hydroxide/Hydrochloric Acid (to adjust pH to ~4-6) | QS |

Process: The gel formulation was prepared by the process as per Example 1. The pH of the mixture was adjusted to 4 to 6 with sodium hydroxide and/or hydrochloric acid and the viscosity of the gel was measured and found to be in the range of about 60,000 to 600,000 cps.

EXAMPLE 3

Diclofenac Sodium 14% w/w Topical Gel

TABLE 3

| Sr. No. | Ingredients | Quantity % w/w |
|---|---|---|
| 1 | Diclofenac Sodium | 14.00 |
| 2 | Carbomer | 2.50 |
| 3 | Edetate Disodium | 0.17 |
| 4 | Methyl paraben | 0.30 |
| 5 | Propyl paraben | 0.08 |
| 6 | Propylene Glycol | 20.00 |
| 7 | Methyl Salicylate | 7.00 |
| 8 | Menthol | 0.3 |
| 9 | Ethyl Alcohol | 5.0 |
| 10 | Purified Water | QS |
| 11 | Sodium Hydroxide/Hydrochloric Acid (to adjust pH to ~4-6) | QS |

Process: Diclofenac sodium, carbomer, edetate sodium and methyl paraben were dissolved in water. Separately, propyl paraben, methyl salicylate and menthol were dissolved in ethyl alcohol. The remainder of the formulation was prepared by the process as per Example 1. The pH of the mixture was adjusted to 4 to 6 with sodium hydroxide and/or hydrochloric acid and the viscosity of the gel was measured and found to be in the range of about 60,000 to 600,000 cps.

What is claimed is:

1. A topical pharmaceutical gel composition suitable for twice daily application of diclofenac comprising:
    at least about 10% w/w of diclofenac sodium;
    about 5-25% w/w of a glycol solvent;
    about 1-6% w/w of at least one gelling agent;
    about 0.01-0.75% w/w of at least one preservative;
    about 0.01-1% w/w of at least one antioxidant;
    about 1-10% w/w of salicylic acid ester;
    about 0.05-1% w/w of menthol;
    at least 50% w/w of water; and
    at least one acidic and/or basic agent to adjust the pH of the composition to 4-8.

2. The gel composition of claim 1, wherein the glycol solvent is selected from the group consisting of propylene glycol, polyethylene glycol, ethylene glycol, butylene glycol, and hexalylene glycol, and mixtures thereof.

3. The gel composition of claim 2, wherein the glycol solvent is propylene glycol.

4. The gel composition of claim 1, wherein the gelling agent is selected from the group consisting of carbomers, xanthan gum, acacia, tragacanth, sodium alginate, gelatin, modified starches, hydroxypropyl cellulose, hydroxyethyl cellulose, hydroxypropyl methylcellulose, hydroxypropyl methylcellulose phthalate, methyl cellulose, co-polymers formed between maleic anhydride and methyl vinyl ether, methacrylate derivatives, polyethylene oxides, polyoxyethylene-polyoxypropylene copolymers, polyvinyl alcohol and mixtures thereof.

5. The gel composition of claim 4, wherein the gelling agent is carbomer.

6. The gel composition of claim 1, wherein the at least one preservative is selected from the group consisting of methyl paraben, propyl paraben, chlorocresol, thomersal, sorbic acid, potassium sorbate and mixtures thereof.

7. The gel composition of claim 1, wherein the antioxidant is selected from the group consisting of edetate disodium, sodium sulphite, sodium metabisulfite, propyl gallate, edetate trisodium, tocopherol derivatives, butylated hydroxyl toluene, butylated hydroxyl anisole, ascorbic acid, fumaric acid, malic acid, and citric acid, and mixtures thereof.

8. The gel composition of claim 1, wherein the antioxidant is edetate disodium.

9. The gel composition of claim 1, wherein the salicylic acid ester is selected from the group consisting of methyl salicylate, ethyl salicylate and glycol monosalicylate, and mixtures thereof.

10. The gel composition of claim 1, wherein the acidic and basic agents are selected from the group consisting of sodium hydroxide, potassium hydroxide, ammonia, hydrochloric acid, acetic acid, lactic acid and citric acid, and mixtures thereof.

11. The gel composition of claim 1, wherein the gel is devoid of either $C_2$ to $C_4$ alkanol, monoalkyl ether of diethylene glycol, or fatty alcohol.

12. The gel composition of claim 1, wherein twice daily application of said gel composition provides steady state blood levels of diclofenac that are comparable to steady state blood levels of diclofenac achieved with 4 times daily application of diclofenac sodium 1% or 3% topical gel.

13. A method for the treatment of painful conditions, inflammations and/or rheumatic diseases comprising topically applying the gel composition of claim 1 to a patient in need thereof.

14. A topical pharmaceutical gel composition suitable for twice daily application of diclofenac or salts consisting of:
about 10-15% w/w of diclofenac sodium as the sole active ingredient;
about 5-25% w/w of propylene glycol;
about 1-6% w/w of carbomer;
about 0.01-0.75% w/w of methyl paraben and propyl paraben;
about 0.01-1% w/w of at least one edetate disodium;
about 1-10% w/w of methyl salicylate;
about 0.05-1% w/w of menthol;
at least 50% w/w of water; and
at least one acidic and/or basic agent to adjust the pH of the composition to 4-8.

15. The topical pharmaceutical gel composition of claim 14, wherein the composition consists of:
about 10% w/w of diclofenac sodium as the sole active ingredient;
about 10% w/w of propylene glycol;
about 3.5% w/w of carbomer;
about 0.4% w/w of methyl paraben and propyl paraben;
about 0.17% w/w of at least one edetate disodium;
about 3% w/w of methyl salicylate;
about 0.2% w/w of menthol;
at least 50% w/w of water; and
at least one acidic and/or basic agent to adjust the pH of the composition to 4-8.

16. The topical pharmaceutical gel composition of claim 14, wherein the composition consists of:
about 14% w/w of diclofenac sodium as the sole active ingredient,
about 20% w/w of propylene glycol,
about 2.5% w/w of carbomer,
about 0.4% w/w of methyl paraben and propyl paraben,
about 0.17% w/w of at least one edetate disodium,
about 7% w/w of methyl salicylate,
about 0.3% w/w of menthol
at least 50% w/w of water; and
at least one acidic and/or basic agent to adjust the pH of the composition to 4-8.

17. A method for the treatment of painful conditions, inflammations and/or rheumatic diseases comprising topically applying twice per day a gel composition to a skin surface of a patient in need thereof, wherein the gel composition consists essentially of diclofenac sodium as the sole active ingredient and the diclofenac sodium is present at a concentration of about 10% w/w to about 15% w/w.

18. The method of claim 17, wherein the diclofenac sodium is present at a concentration of about 10% w/w.

* * * * *